(12) United States Patent
Senoir

(10) Patent No.: US 6,846,331 B2
(45) Date of Patent: Jan. 25, 2005

(54) GRIPPER DEVICE

(75) Inventor: Martin Senoir, Cheshire (GB)

(73) Assignee: Hugh Steeper Limited, Rochester (GB)

(*) Notice: Subject to any disclaimer, the term of this patent is extended or adjusted under 35 U.S.C. 154(b) by 74 days.

(21) Appl. No.: 10/196,417

(22) Filed: Jul. 17, 2002

(65) Prior Publication Data

US 2003/0036805 A1 Feb. 20, 2003

(30) Foreign Application Priority Data

Jul. 17, 2001 (GB) .............................................. 0117383

(51) Int. Cl.[7] .................................................. A61F 2/66
(52) U.S. Cl. ...................................................... 623/57
(58) Field of Search ................... 623/57–65; 294/15–16, 294/25–26, 902; 901/19–24, 30–39

(56) References Cited

U.S. PATENT DOCUMENTS

| | | | | |
|---|---|---|---|---|
| 3,820,168 A | * | 6/1974 | Horvath ......................... | 623/24 |
| 4,302,138 A | * | 11/1981 | Zarudiansky ................... | 414/5 |
| 4,623,354 A | * | 11/1986 | Childress et al. .............. | 623/25 |
| 4,685,925 A | | 8/1987 | Childress et al. | |
| 4,770,662 A | * | 9/1988 | Giampapa ...................... | 623/24 |
| 4,808,187 A | * | 2/1989 | Patterson et al. .............. | 623/25 |
| 5,116,386 A | | 5/1992 | Scribner | |
| 5,252,102 A | * | 10/1993 | Singer et al. .................. | 623/24 |
| 5,336,269 A | * | 8/1994 | Smits ............................ | 623/25 |
| 5,413,611 A | * | 5/1995 | Haslam et al. ................. | 623/25 |
| 5,888,213 A | * | 3/1999 | Sears et al. .................... | 623/24 |
| 6,660,042 B1 | * | 12/2003 | Curcie et al. .................. | 623/24 |

* cited by examiner

Primary Examiner—Alvin Stewart
(74) Attorney, Agent, or Firm—Clark & Brody

(57) ABSTRACT

A gripper device comprising at least two portions which are coupled together and which can be moved towards one another to effect a gripping action and away from one another to effect a release action. An electrical motor is arranged to effect such movement, and a battery is connected to supply electrical current to the motor. A capacitor device is also connected to be capable of supplying electrical current to the electrical motor. A control device is arranged to cause the capacitor device to supply electrical current to the electrical motor after supply of electrical current to the electrical motor by the battery, to increase the strength of the gripping action.

14 Claims, 3 Drawing Sheets

GRIPPER DEVICE

TECHNICAL FIELD

The present invention relates to a gripper device comprising at least two portions which are coupled together and which can be moved towards one another to effect a gripping action and away from one another to effect a release action, an electrical motor arranged to effect such movement, and a battery connected to supply electrical current to the motor.

BACKGROUND ART

Such a gripper device has been used in a band prosthesis which the user can operate to grasp objects. A disadvantage in such a construction is that, in order to increase the strength of the gripping action once the two portions come into contact with the article which is being grasped, it is necessary to use expensive and cumbersome gearing.

SUMMARY OF THE INVENTION

The present invention seeks to obviate this drawback.

Accordingly, the present invention is directed to a gripper device having the construction set out in the opening paragraph of the present specification, further comprising capacitor means also connected to be capable of supplying electrical current to the electrical motor, and control means arranged to cause the capacitor means to supply electrical current to the electrical motor after supply of electrical current to the electrical motor by the battery, to increase the strength of the gripping action.

Advantageously, the gripper device further comprises sensor means having an output and arranged to issue a sensor signal at its output when the two portions are exerting a force beyond a predetermined threshold during a gripping action whilst the battery is supplying electrical current to the electrical motor, the control means have an input connected to the output of the sensor means and are arranged to cause the capacitor means to supply electrical current to the electrical motor upon receipt of a sensor signal. This increases the efficiency of the device by ensuring that the capacitor means are used as soon as the said two portions come into contact with the article which is grasped.

Advantageously, the battery is connected to charge the capacitor. The sensor means may be such as to detect a rise in the electrical current supplied by the battery to the electrical motor. This provides a relatively simple means of determining when the two portions are exerting a force owing to contact between the said two portions and an article which is being gripped.

Alternatively, the sensor means may comprise one or more pressure sensors arranged to provide a sensor signal when the said two portions come into contact with an article which is to be gripped.

Desirably, the gripper device is provided with end-of-movement detector means to detect when the said two parts cease to move relative to one another owing to the gripping action being completed with the article which is being gripped resisting further relative movement of the said two portions towards one another.

To avoid unnecessary loss of energy and undesirable heating up of the component parts of the gripper, it is desirable for the control means to be connected to the end-of-movement detector means and to be so constructed and connected that the control means stop the supply of electrical current from both the battery and the capacitor upon receipt of a signal from the end-of-movement detector means.

Selector means may be available on the control means to select current reversal to effect a release action. input means may be provided as part of the control means to enable the user to control the gripper device.

Preferably, the gripper device forms part of a hand prosthesis.

The capacitor means may comprise a single capacitor or a bank of capacitors. The or each capacitor may comprise a double layer capacitor. The or each capacitor is preferably a supercapacitor. The or each capacitor is preferably an electrochemical capacitor. Desirably, the or each capacitor has a capacitance equal to or greater than 0.1 F.

BRIEF DESCRIPTION OF THE DRAWINGS

An example of a gripper device made in accordance with the present invention will now be described with reference to the accompanying drawings, in which.

DETAILED DESCRIPTION OF THE PREFERRED EMBODIMENTS

Figure 1:
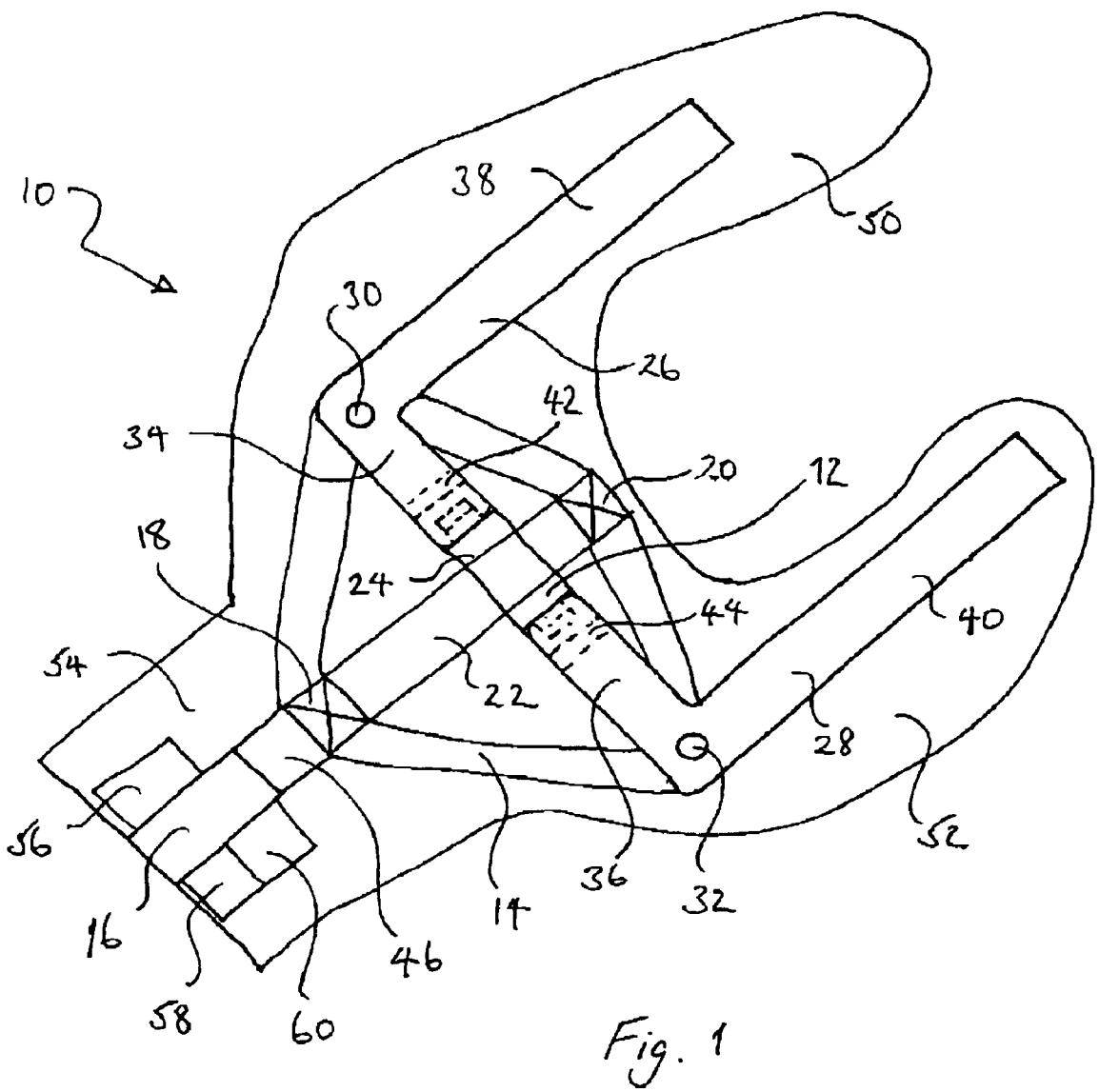
FIG. 1 shows diagrammatically a a gripper device embodying the present invention incorporated in a hand prosthesis.

FIG. 1 shows a hand prosthesis 10 in which is incorporated a gripper device 12. The gripper device 12 comprises a mounting frame or plate 14 secured rigidly to one end of a shaft 16. Two rotary bearings 18 and 20 are fixed to the frame 14 spaced apart along an axis which is co-linear with the shaft 16. A screw threaded rod 22 extends between the bearings 18 and 20 so as to be rotatable about that axis.

A nut 24 is threaded on this screw 22. Two L-shaped members 26 and 28 are pivotably connected at their corners to the frame 14 at pivots 30 and 32 respectively, such that respective limbs 34 and 36 are slidably secured to the nut 24 whilst the other limbs 38 and 40, respectively, of the L-shaped members 26 and 28 extend generally parallel to one another away from the shaft 16.

Slots 42 and 44 are formed in the L-shaped members 26 and 28 where they are slidably attached to the nut 24 to facilitate such sliding whilst inhibiting rotation of the nut.

A motor 46 is secured to the shaft 16 in such a fashion as to be able to rotatably drive the screw threaded rod 22 about its axis.

It will be seen from FIG. 1 that the limb 38 of the L-shaped member 36 is embedded in the digits 50 of the hand prosthesis 10, the limb 40 of the L-shaped member 28 is embedded in the thumb 52 of the hand prosthesis 10, and the shaft 16 is embedded in the wrist 54 of the hand prosthesis 20.

A battery 56, a capacitor 58 and a microprocessor 60 constituting control means of the hand prosthesis 10 are also provided in the wrist 54 of the prosthesis.

Figure 2:
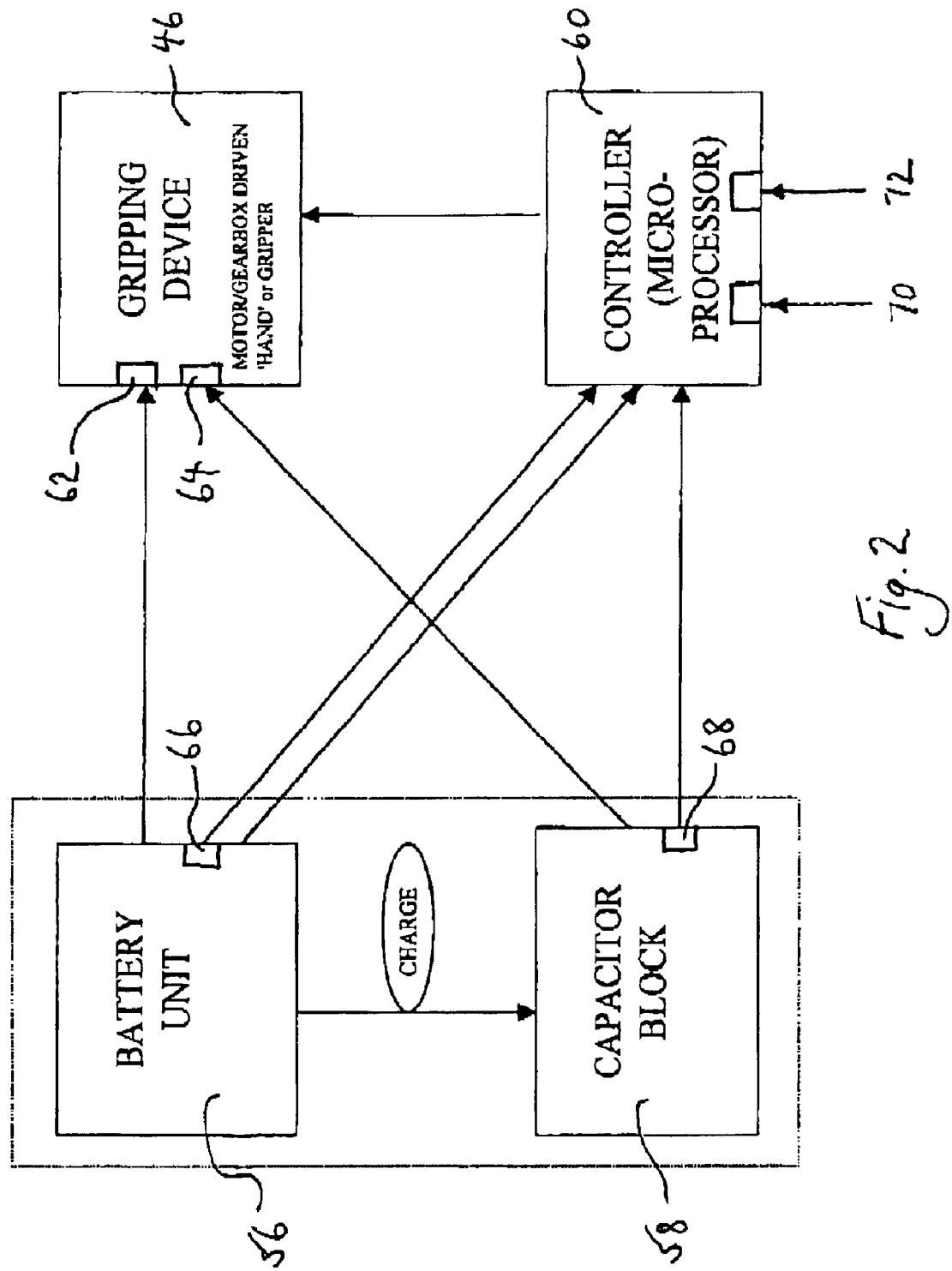
FIG. 2 shows a block circuit diagram showing diagrammatically the circuitry of the device shown in FIG. 1.

The manner in which the different electrical parts of the circuitry of the prosthesis shown in FIG. 1 are connected, as well as certain other auxiliary parts of this circuitry, is shown diagrammatically in FIG. 2.

Thus, as can be seen from FIG. 2, the battery 56 is connected to charge the capacitor 58. Both the battery 56 and the capacitor 58 are connected to the motor 46 via switches 62 and 64, respectively, switchable by a microprocessor 60.

A sensor 66 provided adjacent to the battery 56 detects when the current supplied by the battery 56 to the motor 46 exceeds a certain threshold level, wherever it issues a threshold signal at its output. A connection as illustrated in FIG. 2 from the sensor 66 to the microprocessor 60 enables that signal to be delivered to the microprocessor 60.

A detector 68 is arranged to detect when the current supplied by the capacitor 58 to the motor 46 is sufficiently large to indicate that the limbs 38 and 40 have ceased to move towards one another at the end of a gripping action. A signal indicative of this condition is fed from the detector 68 to the microprocessor 60 by way of a connection therebetween.

The microprocessor 60 is provided with inputs 70 and 72 to enable the user to operate the hand prosthesis, for example by means of vestigial muscles in the stump to which the hand prosthesis is attached operating switching (not shown) to those inputs.

Figure 3:
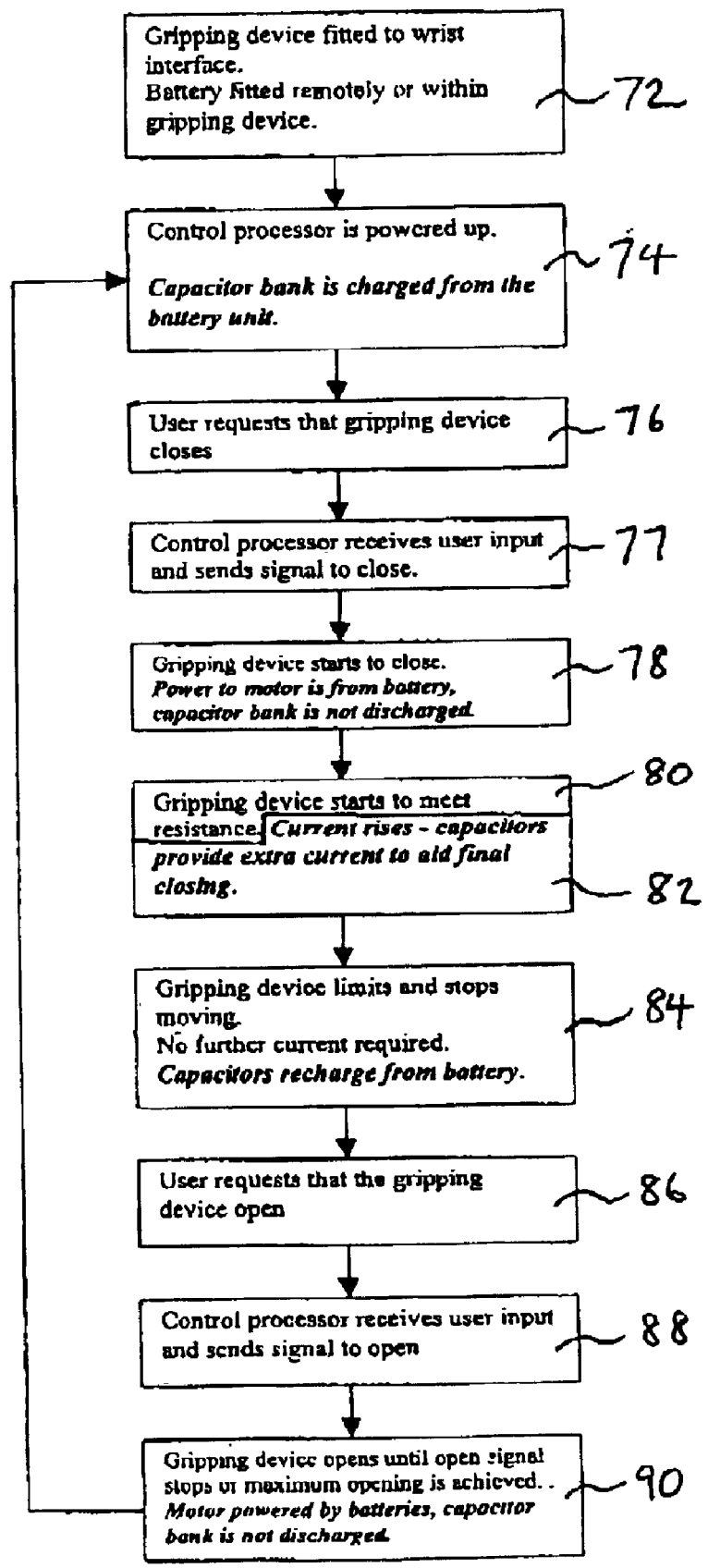
FIG. 3 shows a flow chart of the operation of the gripper device shown in FIG. 1.

The manner of operation of the apparatus is shown in FIG. 3.

Thus, the initial state 72 is in place with the hand prosthesis attached to the user's stump and the battery 56 fitted within the wrist part 54 of the prosthesis 10. The microprocessor 60 is powered-up at step 74, and the capacitor 58 is charged by the battery unit 56.

Step 76 represents the arrival, of a signal at the input 70. This causes the microprocessor 60 to change the setting of the switch 62 at step 77, whereby the gripper device 12 is operated by the switching of the battery 56 to supply electrical current to the motor 46 to effect a gripping action by the gripper device 12.

This brings the gripper device to step 78 in FIG. 3 in which the limbs 38 and 40 move towards one another at the start of a gripping action, with the motor 46 being powered by the battery 56. At step 80, the gripping device 12 starts to encounter resistance to further gripping action by the article that is being gripped. As a result, the current supplied by the battery unit 56 to the motor 46 rises until a signal is triggered by a sensor 66 to the microprocessor 60. Upon receipt of such a signal, the microprocessor 60 causes the setting of the switch 64 to be changed at step 82, whereby an electrical current is delivered from the capacitor 58 to the motor 46 via the switch 64.

A point is reached at step 84 when the motor 46 can no longer drive the limbs 38 and 40 any closer together even with the additional current provided by the capacitor 58. This is indicated by the end-of-movement detector 68, which detects when the current supplied by the capacitor 58 to the motor 46 exceeds a given threshold value. The detector 68 provides the microprocessor 60 with a signal accordingly. As a result, the microprocessor 60 issues signals to change the settings of the switches 62 and 64, to prevent further current being supplied to the motor 46 from either the battery 56 or the capacitor 58. Because of the screw-threaded rod and nut construction of the gripper device 12, the grip of the gripper device 12 is not released at this stage.

Such release does not occur until step 86 when the user sends a signal to the input 72 of the microprocessor 60, whereupon the switch 62 is switched by the microprocessor 60 to connect the battery 56 to the motor 46 for reverse drive. This occurs at step 88 in FIG. 3. Again, upon indication from the sensor 66 when the gripper device 12 is fully open, the microprocessor 60 opens the switch 62 to stop further supply of current from the battery 56 to the motor 46. This occurs at step 90 in FIG. 3. The procedure then reverts to step 74 in FIG. 3 to commence a further grip and release cycle when the user is ready.

The capacitor 58 may be a type DYNACAP double layer capacitor of 1F, being Part No. DZ-2R5D105N manufactured by Elna of Japan. Alternatively, the capacitor may be a 5F type ULTRACAP double layer capacitor of the B49100 series, being Part No. B4900-A1503-Q000, manufactured by Epcos of Germany.

Numerous variations and modifications to the illustrated design of gripper device may be made without taking the resulting construction outside the scope of the present invention. For example, a contra-rotating gear construction could be used to move the limbs 38 and 40 towards and away from one another instead of the screw-threaded rod and nut assembly shown in FIG. 1.

It will be appreciated that the invention is not restricted to hand prosthesis but may be used for robots or indeed any other application where a gripping action is required.

Means (not shown) may be provided to restrict the maximum current available from the capacitor 58, and means (not shown) may also be provided to limit the duration for which the capacitor 58 is connected to drive the motor 46, thus prolonging battery life and limiting thermal stresses to the motor 46. Such time limiting means may be used instead of the end-of-movement detector 68.

The battery 56, the capacitor 58 and the microprocessor 60 may be located more remotely from the hand, for example in an arm prosthesis, if space is not available in the hand prosthesis, for example if it is a child's hand prosthesis.

The battery 56, capacitor 58 and microprocessor 60 may also be provided in a single battery pack suitable for retro-fitting in existing prostheses.

Means (not shown) may be provided to limit the duration of operation of the supply of electrical current to the electrical motor 46 by the battery 56 before the capacitor 58 is used for that purpose, instead of using the sensor 66.

I claim:

1. A gripper device comprising at least two portions which are coupled together and which can be moved towards one another to effect a gripping action and away from one another to effect a release action, an electrical motor arranged to effect such movement, and a battery connected to supply electrical current to the motor, wherein the gripper device further comprises a capacitor device also connected to be capable of supplying electrical current to the electrical motor, and a control device arranged to cause the capacitor device to supply electrical current to the electrical motor after an initial supply of electrical current to the electrical motor by the battery to increase the strength of the gripping action.

2. A gripper device according to claim 1, wherein the gripper device further comprises a sensor device having an output and arranged to issue a sensor signal at its output when the said two portions are exerting a force beyond a predetermined threshold during a gripping action whilst the battery is supplying electrical current to the electrical motor, and the control device has an input connected to the output of the sensor device and is arranged to cause the capacitor device to supply electrical current to the electrical motor upon receipt of a sensor signal.

3. A gripper device according to claim 2, wherein the sensor device is such as to detect a rise in the electrical current supplied by the battery to the electrical motor.

4. A gripper device according to claim 2, wherein the sensor device comprises at least one pressure sensor arranged to provide a sensor signal when the said two portions come into contact with an article which is to be gripped.

5. A gripper device according to claim 1, wherein the gripper device is provided with an end-of-movement detector device to detect when the said two parts cease to move relative to one another owing to the gripping action being completed with the article which is being gripped resisting further relative movement of the said two portions towards one another.

6. A gripper device according to claim 5, wherein the control device is connected to the end-of-movement detector device and is so constructed and connected that the control device stops the supply of electrical current from both the battery and the capacitor device upon receipt of a signal from the end-of-movement detector device.

7. A gripper device according to claim 1, wherein a selector device is provided on the control device to select current reversal to effect a release action.

8. A gripper device according to claim 1, wherein at least one input is provided as part of the control device to enable the user to control the gripper device.

9. A gripper device according to claim 1, wherein the gripper device forms part of a hand prosthesis.

10. A gripper device according to claim 1, wherein the capacitor device comprises at least one double layer capacitor.

11. A gripper device according to claim 1, wherein the capacitor device comprises at least one supercapacitor.

12. A gripper device according to claim 1, wherein the capacitor device comprises at least one electrochemical capacitor.

13. A gripper device according to claim 1, wherein the capacitor device comprises at least one capacitor having a capacitance equal to or greater than 0.1 F.

14. A gripper device according to claim 1, wherein the battery is connected to charge the capacitor device.

* * * * *